(12) United States Patent
Fleischer et al.

(10) Patent No.: US 7,946,153 B2
(45) Date of Patent: May 24, 2011

(54) METHOD FOR MEASURING GASES AND/OR MINIMIZING CROSS SENSITIVITY IN FET-BASED GAS SENSORS

(75) Inventors: Maximilian Fleischer, Höhenkirchen (DE); Uwe Lampe, Buxtehude (DE); Hans Meixner, Haar (DE); Roland Pohle, Herdweg (DE); Elfriede Simon, München (DE)

(73) Assignee: Micronas GmbH, Freiburg (DE)

( * ) Notice: Subject to any disclaimer, the term of this patent is extended or adjusted under 35 U.S.C. 154(b) by 969 days.

(21) Appl. No.: 11/587,173

(22) PCT Filed: Apr. 22, 2005

(86) PCT No.: PCT/EP2005/004318
§ 371 (c)(1),
(2), (4) Date: Dec. 13, 2006

(87) PCT Pub. No.: WO2005/103668
PCT Pub. Date: Nov. 3, 2005

(65) Prior Publication Data
US 2008/0016949 A1    Jan. 24, 2008

(30) Foreign Application Priority Data
Apr. 22, 2004   (DE) .................. 10 2004 019 604

(51) Int. Cl.
*G01N 7/00* (2006.01)
(52) U.S. Cl. .................................... 73/31.05
(58) Field of Classification Search .............. 73/31.05
See application file for complete search history.

(56) References Cited

U.S. PATENT DOCUMENTS 3,663,870 A    5/1972   Tsutsumi et al.
(Continued)

FOREIGN PATENT DOCUMENTS

DE    2947050    11/1979
(Continued)

OTHER PUBLICATIONS

Paris et al., "57.5: Low Drift Air-Gap CMOS-FET Gas Sensor," Proceedings of IEEE Sensors, vol. 1 of 2, Conf. 1, Jun. 12, 2002, pp. 421-425, 2002, XP010605129, ISBN: 0-7803-7454-1.
(Continued)

*Primary Examiner* — Hezron Williams
*Assistant Examiner* — Rodney T Frank
(74) *Attorney, Agent, or Firm* — Muncy, Geissler, Olds & Lowe, PLLC

(57) ABSTRACT

A gas sensor based on a field effect transistor ("FET") evaluates both a change in work function of a gas-sensitive layer of the FET and a change in the capacitance of the layer. Thus, two physically independent signals are read from the gas-sensitive layer, each signal representing a sensitivity to a different gas. This reduces the effect of cross-sensitivities; that is, of one gas on the target gas. The underlying physical mechanisms, the first causing a change in the work function in a reaction with gases and the second causing a change in the capacitance of the sensitive layer, are widely different. Because of this, the two parameters demonstrate different gas sensitivities. If the reactions to both gases are known, the effect of the interfering gas on the sensor signal can be compensated for, and with this the concentration of the target gas can be determined.

16 Claims, 2 Drawing Sheets

U.S. PATENT DOCUMENTS

| | | | |
|---|---|---|---|
| 4,023,549 | A | 5/1977 | Hewitt |
| 4,151,060 | A | 4/1979 | Isenberg |
| 4,198,851 | A * | 4/1980 | Janata .................. 73/31.06 |
| 4,354,308 | A | 10/1982 | Shimada et al. |
| 4,633,704 | A | 1/1987 | Tantram et al. |
| 4,638,346 | A | 1/1987 | Inami et al. |
| 4,792,433 | A | 12/1988 | Katsura et al. |
| 4,878,015 | A * | 10/1989 | Schmidt et al. .............. 324/71.5 |
| 5,635,628 | A | 6/1997 | Fleischer et al. |
| 5,879,527 | A | 3/1999 | Kiesele et al. |
| 6,041,643 | A | 3/2000 | Stokes et al. |
| 6,454,834 | B1 | 9/2002 | Livingstone et al. |
| 6,566,894 | B2 | 5/2003 | Rump |
| 6,935,158 | B2 | 8/2005 | Serina et al. ................. 73/31.05 |
| 2002/0092974 | A1 | 7/2002 | Kouznetsov |
| 2004/0112764 | A1 | 6/2004 | Stokes et al. .................. 205/782 |
| 2004/0133116 | A1 | 7/2004 | Abraham-Fuchs et al. |
| 2005/0035808 | A1 | 2/2005 | Frerichs |

FOREIGN PATENT DOCUMENTS

| | | |
|---|---|---|
| DE | 4028062 | 9/1990 |
| DE | 4105598 | 9/1992 |
| DE | 4239319 | 4/1993 |
| DE | 43 33 875 | 4/1995 |
| DE | 19534557 | 3/1997 |
| DE | 19613274 | 10/1997 |
| DE | 197 08 770 | 8/1998 |
| DE | 10245947 | 4/2004 |
| EP | 0952447 | 4/1998 |
| EP | 0 947 829 | 10/1999 |
| EP | 1 059 528 | 5/2000 |
| EP | 1104884 | 11/2000 |
| EP | 1103809 | 5/2001 |
| EP | 1 176 418 | 1/2002 |
| JP | 60242354 | 12/1985 |
| JP | 01059049 | 3/1989 |
| JP | 03131749 | 6/1991 |
| JP | 03259736 | 11/1991 |
| WO | WO 96/01992 | 1/1996 |
| WO | WO 98/41853 | 9/1998 |
| WO | WO 03/050526 | 6/2003 |

OTHER PUBLICATIONS

Burgmair et al., "Humidity and temperature compensation in work function gas sensor FETs," Sensors and Actuators B, Elsevier Sequoia S.A., Lausanne, CH, vol. 93, No. 1-3, pp. 271-275, 2003.

Burgmair et al., "Field effect transducers for work function gas measurements : device improvements and comparison of performance," Sensors and Actuators B, Elsevier Sequoia S.A., Lausanne, CH, vol. 95, No. 1-3, pp. 183-188, 2003.

Gergintschew et al., "The capacitively controlled field effect transistor (CCFET) as a new low power gas sensor," Sensors and Actuators B, Elsevier Sequoia S.A., Lausanne, CH, vol. 36, No. 1, pp. 285-289, 1996.

Covington, et al. "Combined smart chemFET/resistive sensor array," Proceedings of the IEEE, vol. 2., pp. 1120-1123, 2003.

Kienle et al., "Acticated Charcoal and its Industrial Application," Stuttgart : Enke, ISBN 3-432-90881-4, pp. 126 and 162-163, 1980.

Müller et al., "Adsorber for a Low Solvent Load," Intelligent Exhaust Air Cleaning Using Electric Current, Verfahrenstechnik, vol. 37, No. 9, pp. 30-31, 2003.

CCI Charcoal International : Activated Charcoal Textiles Given Uniform Brand Name of Zorflex, MaschinenMarkt, 2004, No. 17, p. 89.

Leu et al., "Evaluation of gas mixtures with different sensitive layers incorporated in hybrid FET structures," Sensors and Actuators B, Elsevier Sequoia, vol. 18-19, 1994, pp. 678-681.

Wöllenstein et al., "Cobalt oxide based gas sensors on silicon substrate for operation at low temperatures," Sensors and Actuators B: Chemical, Elsevier Sequoia, vol. 93, No. 1-3, Aug. 2003, pp. 442-448.

Fleischer et al., "Selective gas detection with high-temperature operated metal oxides using catalytic filters," Sensors and Actuators B, vol. 69, pp. 205-210, 2000.

Pohle et al., "Realization of a New Sensor Concept: Improved CCFET and SGFET Type Gas Sensors in Hybrid Flip-Chip Technology," Transducers, 12th International Conference on Solid-State Sensors, Actuators and Microsystems, Jun. 2003, vol. 1, 9, pp. 135-138.

Peschke et al., "Optimization of Sputtered SnO2 Films as Gas-sensitive Layers for Suspended-gate FETs", Sensors and Actuators B, 1991, pp. 157-160, XP-002379749.

Lampe et al., "GasFET for the detection of reducing gases", Sensors and Actuators B 111-112, 2005, pp. 106-110.

Mizsei et al., "Simultaneous Response of Work Function and Resistivity of some SnO2-based Samples to H2 and H2S", Sensors and Actuators B, 4 (1991), pp. 163-168, XP-002379750.

Doll et al., "Gas detection with work function sensors", Proceedings of the SPIE, SPIE, Bellingham, VA, US, vol. 3539, Nov. 1998, pp. 96-105, XP-002329891.

Paris et al., "57.5: Low Drift Air-Gap CMOS-FET Gas Sensor," Proceedings of IEEE Sensors, vol. 1 of 2, Conf. 1, Jun. 12, 2002, pp. 421-425, 2002, XP010605129, ISBN: 0-7803-7454-1.

Doll et al., "Modular System Composed of Hybrid GasFET Modules," ITG-Technical Report 126: Sensors-Technology and Application, VDE Verlag, Berlin, Germany, 1994, pp. 465-470, XP-000874734.

M. Lehmann, "Nanometre Dimensions in Bio and Gas Sensor Technology", MST News, Mar. 2004, pp. 43-47, XP-002379751.

* cited by examiner

METHOD FOR MEASURING GASES AND/OR MINIMIZING CROSS SENSITIVITY IN FET-BASED GAS SENSORS

PRIORITY INFORMATION

This patent application claims priority from International patent application PCT/EP2005/004318 filed Apr. 22, 2005 and German patent application 10 2004 019 604.4 filed Apr. 22, 2004, which are hereby incorporated by reference.

BACKGROUND OF THE INVENTION

This invention relates in general to gas sensors and in particular to a method for improving the selectivity of FET-based gas sensors such that interfering effects of cross-sensitivities are minimized.

Gas sensors that utilize and evaluate the change in work function of sensitive materials as a physical parameter have been experiencing increased interest recently. The reasons for this are the ability to operate such sensors with relatively low operating energy (low operating power), the economical production and construction technology of such gas sensors (low production costs), and a broad palette of gases that can be detected with this platform technology (high versatility). Numerous different detection substances can be integrated into such structures. Their construction and mode of operation are disclosed, for example, in German Patent Applications 19814857, 19956744, 19849932 and 19956806. A number of materials can be used for sensitive layers in such gas sensors.

The basic structure of these prior art work function gas sensors is shown in FIG. 2, which schematically illustrates the structure of the work function of such a sensor with FET readout, particularly an SGFET (suspended gate field effect transistor).

In the presence of the gas to be detected, an electrical potential that corresponds to the change in the work function of the sensitive layer (typically 50-100 mV) is developed on the sensitive layer which is coated on the bottom of the raised gate electrode. This potential acts on the channel of the FET structure and changes the source-drain current. The changed source-drain current is measured directly. Alternatively, the change in source-drain current is restored by applying an additional voltage to the suspended gate or to the transistor trough. The additionally applied voltage represents a readout signal that directly correlates with the change in work function of the sensitive layer.

A basic problem with all gas sensors including the type described above is their relatively limited selectivity. In other words, the sensors under some circumstances react not only to the target gas but also to other gases, which is called cross-sensitivity. The superimposed gas signals then lead in many applications to a situation in which the target gas concentration cannot be determined with adequate reliability from the sensor signal, since the sensor signal is distorted in an unacceptable amount by the cross-sensitivity. Up to now, it has been necessary to accept the distortion of the sensor signal. The distortion effect can be partially eliminated by intelligent signal evaluation adapted to the application, but this possibility is relatively limited for many applications. Alternatively, an additional sensor can be used that is sensitive specifically to the interfering gas and whose additional signal is used to compensate for the interference effect in an appropriate signal processor. However, this approach involves substantially higher system costs.

What is needed is an FET-based gas sensor having relatively reduced distortion of the sensor signal due to cross-sensitivity.

SUMMARY OF THE INVENTION

The invention is based on the recognition that the effect of cross-sensitivities can be sharply reduced by using an FET-based gas sensor in which not only the change in work function of a gas-sensitive layer (change in interface potential), but also the change in the capacitance of the gas-sensitive layer is evaluated. In this way, two physically independent signals are read from the gas-sensitive layer, which can each represent a sensitivity to a different gas.

The underlying physical mechanisms, the first causing a change in the work function in a reaction with gases, and the second causing a change in the capacitance of the sensitive layer, are widely different. Because of this, the two parameters demonstrate different gas sensitivities. In other words, the reactions to the target gas and to the interfering gas are different. Then if the reactions to both gases are known, the effect of the interfering gas on the signal can be compensated for, and with this the concentration of the target gas can be determined. Alternatively, both gas concentrations can also be calculated.

In accordance with the invention, essentially there are two sensors in one. That is, two independent signals have been generated by the manner of operation in one sensor structure. This saves the costs of not having a second sensor structure. In addition, gas sensors are subject to drift effects in long-term operation. Two separate sensor structures have a stronger tendency under some circumstances toward different drift phenomena than one sensor structure, which makes it difficult to compensate for the errors in the signal processor. Other advantages include additional data that can be read out of the system, but with the need for only one sensor structure.

These and other objects, features and advantages of the present invention will become more apparent in light of the following detailed description of preferred embodiments thereof, as illustrated in the accompanying drawings.

DETAILED DESCRIPTION OF THE INVENTION

Figure 1:
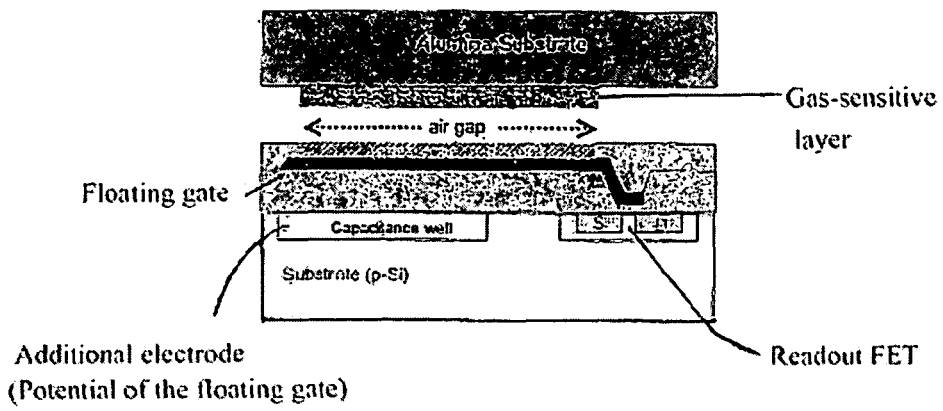
FIG. 1 illustrates the structure of a CCFET-type gas sensor.
Figure 2:
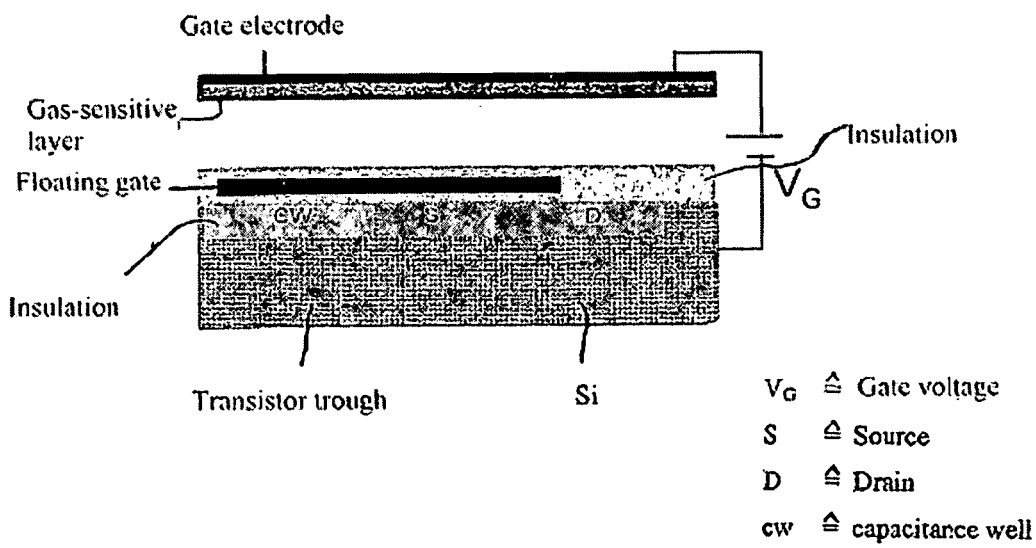
FIG. 2 illustrates schematically the structure of a prior art work function gas sensor with an FET readout.

Both classical suspended gate FET gas sensors (SGFETs) with a structure corresponding to FIG. 2, and gas FETs in which the capacitance is developed by the gas-sensitive layer and the air gap and the electrical potential is transmitted to a separately attached readout FET through an electrically conductive connection (CCFETs), corresponding to FIG. 1, are suitable for the present invention. The invention is also suitable for all other constructions with similar functionality.

In the SGFET structure of FIG. 2, the action of interface potentials on channel conductivity (i.e., the source-drain current) is read in the described operation. The capacitance of the sensitive layer is read out by applying alternating voltage (typically 10-10,000 Hz) to the gate electrode. The coupling of the gate voltage to the channel conductivity changes as a function of the capacitance of the sensitive layer. In other words, the alternating portion of the source-drain current brought about by the alternating voltage on the gate depends on the capacitance of the gas-sensitive layer and is thus a direct measure of this capacitance.

If the gate voltage is kept constant for specific application-related reasons, an alternating voltage can alternatively be applied to the transistor itself, i.e. to the bulk connection of the silicon or to the transistor trough in case of a corresponding structure. The basic function with this procedural method is the same as described above.

With a CCFET structure in which still another electrode, called a capacitance well, is attached below the floating gate, the alternating voltage can also be applied as described above through the top contact face of the sensitive layer, and also through the transistor. With this variant of gas sensor, however, the alternating voltage can beneficially be introduced through the capacitance well. This variant avoids both an excessively severe change in potential conditions in the air gap and impairments caused by applying potentials to the transistor. This also applies similarly to the variant of the SGFET known as the FGFET, as illustrated in FIG. 2.

With respect to all variations of the present invention, an alternating voltage can be used either for capacitance readout simultaneously with the readout of the interface potential, with both the alternating and constant fractions of the source-drain current then being read, or with alternation between the two operating modes. It is not absolutely necessary to use an alternating voltage on the gate. Alternatively, a rapid change in potential can occur. The time curve of the action of this potential change on the source-drain current in this case likewise depends on the capacitance of the sensitive layer and can be utilized in precisely the same way to determine the capacitance. Alternatively, the transistor characteristic (i.e., the change of source-drain current with gate voltage) can also be evaluated. Since the resulting transistor slope is also determined by the air gap capacitances, this is directly dependent on the capacitance of the sensitive layer.

For use with gas-sensitive materials having different morphologies, a distinction is made between porous, or open-pored materials, and solid, continuous or closed-pored materials. With porous materials, there is often a relatively strong cross-effect of varying atmospheric humidity. This results from the deposition of moisture on the grains and causes a sharp change in capacitance of the porous layer. An example of this is $BaCO_3$, which is prepared as an open-pored layer. This is characterized by relatively high sensitivity of the sensor material to $CO_2$, a potential occurring from a change in work function on the outer boundary of the layer, which is independent of layer thickness. It is also characterized by cross-sensitivity to moisture that occurs from changes of capacitance in the pores of the layer, and therefore depends linearly on the layer thickness.

In a mixed readout, humidity changes can modify the useful signal to $CO_2$ in an unacceptable way. If the capacitance is then read separately according to the invention, it is possible to make a correction of the measurement from the separately obtained moisture signal.

Other $CO_2$-sensitive materials such as $BaTiO_3$ or material variants doped with CuO, or all other porous sensor materials, can beneficially be utilized in a comparable way.

With respect to non-porous materials, the mechanism producing essentially moisture effects does not prevail. Here also, however, depending on the type of gas and the detection material, there are different effects of various gases on work function and capacitance. The former ordinarily occur from interface reactions of the gases, and the latter from reactions of the gas in the interior of the sensor layer.

This change in capacitance described above can be caused, for example, by a change in thickness and/or modification of the dielectric constant of the sensitive layer.

Figure 3:
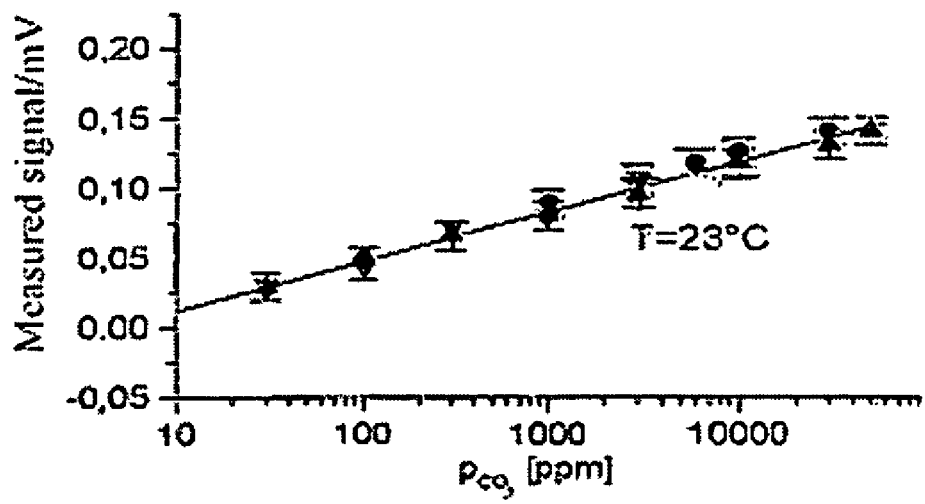
FIGS. 3 and 4 illustrate graphs of gas reactions with the mixed readout principle according to the invention on an FET.
Figure 4:
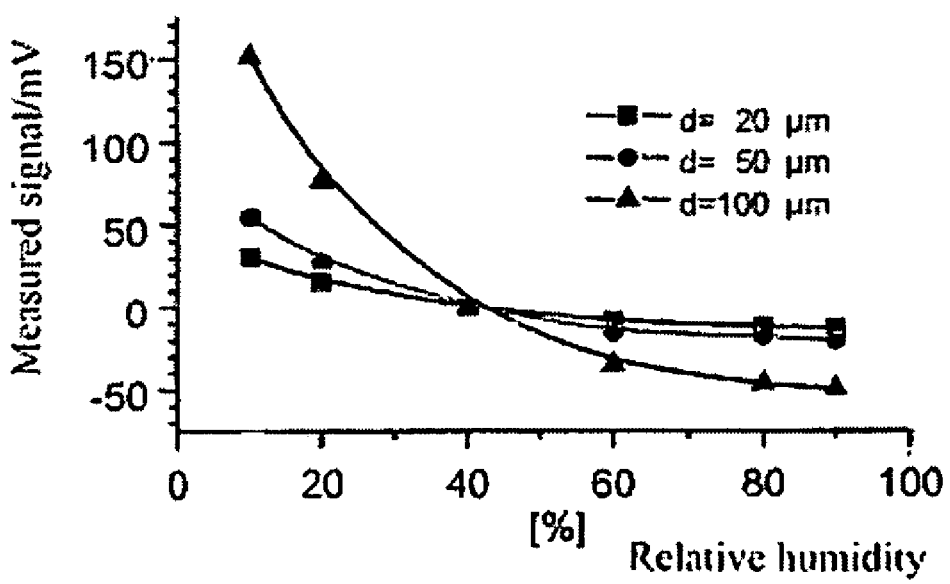

FIGS. 3 and 4 illustrate graphs of gas reactions with the mixed readout principle on a FET according to the invention.

Although the present invention has been illustrated and described with respect to several preferred embodiments thereof, various changes, omissions and additions to the form and detail thereof, may be made therein, without departing from the spirit and scope of the invention.

What is claimed is:

1. A method for determining a concentration of a target gas using a field effect transistor (FET)-based gas sensor having a gas-sensitive layer, the method comprising the steps of:
   evaluating a change in capacitance of the gas-sensitive layer, the change in the capacitance relating to a concentration of a gas other than the target gas;
   evaluating a change in work function of the gas-sensitive layer, the change in the work function relating to the concentration of the target gas; and
   determining the concentration of the target gas based on the change in work function and the change in capacitance of the gas-sensitive layer.

2. the method of claim 1, where the step of evaluating a change in capacitance of the gas-sensitive layer comprises the steps of:
   applying an alternating voltage to a gate electrode of the FET; and
   determining the capacitance of the gas-sensitive layer from an electrical current between source and drain portions of the FET.

3. The method of claim 2, where the alternating voltage is applied trough one of the gas-sensitive layer, a capacitance well of the FET, and a transistor trough.

4. The method of claim 2, where a time curve of the potential change on the current between the source and drain portions of the FET is used to determine the capacitance of the gas-sensitive layer.

5. The method of claim 2, where the change of the current between the source and drain portions of the FET with respect to the voltage applied to the gate electrode is used to determine the capacitance of the gas-sensitive layer.

6. The method of claim 1, where the step of evaluating a change in capacitance of the gas-sensitive layer comprises the steps of:
   applying a constant voltage to a gate electrode of the FET;
   applying an alternating voltage to one of a transistor trough, a bulk silicon of the FET, and the capacitance well; and
   determining the capacitance of the gas-sensitive layer from an electrical current between source and drain portions of the FET.

7. The method of claim 1, where the step of evaluating a change in capacitance of the gas-sensitive layer comprises the steps of:
   applying a changing voltage to a gate electrode of the FET;
   applying an alternating voltage to one of a transistor trough, a bulk silicon of the FET, and the capacitance well; and
   determining the capacitance of the gas-sensitive layer from an electrical current between source and drain portions of the FET.

8. A method for reducing the effect of cross-sensitivity of a first gas on a target gas in a field effect transistor (FET)-based gas sensor having a sensitive layer, the method comprising the steps of:
   determining a change in capacitance of the sensitive layer;

determining a change in the work function on the sensitive layer; and determining a concentration of the target gas based on the determined change in work function and the determined change in the capacitance of the sensitive layer.

9. The method of claim 8, where the step of determining any change in capacitance of the sensitive layer comprises the steps of:

applying an alternating voltage to a gate electrode of the FET; and determining the capacitance of the sensitive layer from an electrical current between source and drain terminals of the FET.

10. The method of claim 9, where the alternating voltage is applied trough one of the sensitive layer, a capacitance well of the FET, and a transistor trough.

11. The method of claim 9, where a time curve of the potential change on the current between the source and drain portions of the FET is used to determine the capacitance of the sensitive layer.

12. The method of claim 9, where the change of the current between the source and drain terminals of the FET with respect to the voltage applied to the gate electrode is used to determine the capacitance of the sensitive layer.

13. The method of claim 8, where the step of evaluating a change in capacitance of the gas-sensitive layer comprises the steps of:

applying a constant voltage to a gate electrode of the FET;

applying an alternating voltage to one of a transistor trough, a bulk silicon of the FET, and the capacitance well; and determining the capacitance of the gas-sensitive layer from an electrical current between source and drain portions of the FET.

14. The method of claim 8, where the step of determining any change in capacitance of the sensitive layer comprises the steps of:

applying an constant voltage to a gate electrode of the FET;

applying an alternating voltage to one of a transistor trough, a bulk silicon of the FET, and the capacitance well; and determining the capacitance of the sensitive layer from an electrical current between source and drain terminals of the FET.

15. The method of claim 8, where the step of determining any change in capacitance of the sensitive layer comprises the steps of:

applying an changing voltage to a gate electrode of the FET; and determining the capacitance of the sensitive layer from an electrical current between source and drain terminals of the FET.

16. A method for determining a concentration of a target gas using a field effect transistor (FET)-based gas sensor having a gas-sensitive layer, the method comprising the steps of:

evaluating a change in capacitance of the gas-sensitive layer, the change in the capacitance relating to a concentration of a gas other than the target gas;

evaluating a change in work function of the gas-sensitive layer, the change in the work function relating to the concentration of the target gas and being influenced by a gas other than the target gas; and determining the concentration of the target gas based on the change in work function and the change in capacitance of the gas-sensitive layer.

* * * * *